United States Patent
Lee et al.

(10) Patent No.: US 6,770,671 B2
(45) Date of Patent: Aug. 3, 2004

(54) 7,8-DIHYDRO-XANTHENONE-8-CARBOXYLIC ACID DERIVATIVE AND NOVEL MICROBE PRODUCING THE SAME

(75) Inventors: Jung Joon Lee, Taejon-si (KR); Jeong-Hyung Lee, Taejon-si (KR); Hang Sub Kim, Taejon-si (KR); Young-Soo Hong, Taejon-si (KR); Yun Joo Park, Taejon-si (KR)

(73) Assignee: Korea Research Institute of Bioscience and Biotechnology (KR)

( * ) Notice: Subject to any disclaimer, the term of this patent is extended or adjusted under 35 U.S.C. 154(b) by 0 days.

(21) Appl. No.: 10/220,724

(22) PCT Filed: Mar. 8, 2001

(86) PCT No.: PCT/KR01/00358
§ 371 (c)(1),
(2), (4) Date: Sep. 4, 2002

(87) PCT Pub. No.: WO01/66783
PCT Pub. Date: Sep. 13, 2001

(65) Prior Publication Data
US 2003/0073735 A1 Apr. 17, 2003

(30) Foreign Application Priority Data
Mar. 8, 2000 (KR) ........................................ 2000-11563

(51) Int. Cl.[7] .............................................. A61K 31/35
(52) U.S. Cl. ...................... 514/455; 549/391
(58) Field of Search ........................... 514/455; 549/391

(56) References Cited

FOREIGN PATENT DOCUMENTS

| EP | 0 652 000 A1 | 10/1994 |
|---|---|---|
| WO | WO 99/26622 | 6/1999 |

*Primary Examiner*—Amelia Owens
(74) *Attorney, Agent, or Firm*—Muserlian, Lucas & Mercanti, LLP

(57) ABSTRACT

Disclosed are a novel compound represented by the following chemical formula (1), useful for the prophylaxis and treatment of angiogenic diseases, its production, and a novel microorganism producing the same. Aspergillus sp. Y80118 isolated from soil was found to produce 7,8-dihydro-1,7-dihydroxy-3-hydroxymethyl-xanthenone-8-carboxylic acid methylester which inhibits VEGF-induced proliferation of HUVEC, angiogenesis in CAM assay, and tumor growth. The novel compound can be effectively used for the medical treatment of anigiogenic diseases, including cancers, rheumatoid arthritis, and diabetic retinopathy.

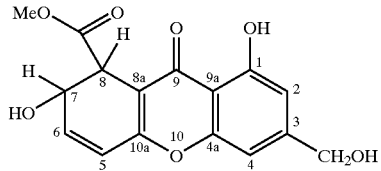

<1>

4 Claims, 3 Drawing Sheets

7,8-DIHYDRO-XANTHENONE-8-CARBOXYLIC ACID DERIVATIVE AND NOVEL MICROBE PRODUCING THE SAME

FIELD OF THE INVENTION

This patent application claims a benefit of priority from Korean Patent Application No. 2000/11563 filed Mar. 8, 2000 through PCT application Ser. No. PCT/KR01/00358 filed Mar.8, 2001, the contents of each of which are incorporated herein by reference.

The present invention relates to a novel 7,8-dihydro-xanthenone-8-carboxylic acid derivative, the preparation thereof, and pharmaceutical compositions comprising the 7,8-dihydro-xanthenone-8-carboxylic acid derivative as a pharmaceutically active ingredient. More particularly, the present invention relates to a 7,8-dihydro-xanthenone-8-carboxylic acid derivative, which inhibits angiogenesis and tumor growth, a method for preparing such a compound from fungi, and pharmaceutical compositions comprising such a compound as a pharmaceutically active ingredient, which are effective for the treatment of angiogenic diseases, such as cancers, rheumatoid arthritis and diabetic retinopathy.

BACKGROUND

Cancer, one of the most intractable diseases, has been extensively studied to develop anti-cancer agents. The most of anti-cancer agents developed thus far are, however, low specific for cancer cells, so as to cause serious side effects. Further, owing to their heterogeneity and genetic instability, cancer cells acquire resistance to the anti-cancer agents. Taking advantage of recent advances in our understanding of angiogenesis in tumors, research all over the world has been directed toward the development of anti-angiogenic agents to solve the conventional problems of anti-cancer agents.

Angiogenesis is a complex process in which capillary blood vessels grow in a complex physiological processes (J. Folkman and M. Klagsbrun, Science, 235, 442–447, 1987); J. Folkman and Y. Shing, J. Biol. Chem., 267, 10931–10934, 1992). Angiogenesis is driven by a complex array of soluble mediators, matrix molecules and accessory cells that function to fine-tune and coordinate the response in both time and space. The initiation of angiogenesis is mediated by multiple molecules that are released from a number of sources including inflammatory cells, such as mast cells and macrophage as well as a variety of tumor cells. These molecules activate the normally quiescent vascular endothelium by binding to their respective receptors. These activated endothelial cells have a characteristic set of traits which include increased cellular proliferation, elevated expression of cell adhesion molecules, increased secretion of proteolytic enzymes, increased cellular migration and invasion, and differentiation to capillary tube. These complex cellular processes should be successfully accomplished to complete angiogenesis.

The relation between cancer and angiogenesis has been studied since Dr. Judah Folkman has hypothesized in 1971 that angiogenesis might be indispensable for the growth of tumors (J. Folkman, New England Journal of Medicine, 285, 1182–1186, 1971). Solid tumors can not grow beyond the size of 1–2 mm without inducing the formation of new blood vessels to supply needs of the tumor such as growth factors, oxygen and nutrients. Accordingly, blocking the angiogenesis around tumors can inhibit the growth and metastasis of tumors. In 1990, it was also found that fumagillin, a naturally occurring compound, inhibits angiogenesis (D. Ingber, T. Fujita, et al., Nature, 348, 555–557, 1990). Since then, much attention has been paid to the development of novel angiogenesis inhibitors. For instance, angiostatin (M. S. O'Reilly et al., Cell, 79, 315–328, 1994) and endostatin (M. S. O'Reilly et al., Cell, 88, 277–285, 1997), both endogenous angiogenesis inhibitors, have recently been proven to have potent anti-cancer activity in animal tests, attracting more attention to angiogenesis inhibitors as anti-cancer agents.

Angiogenesis inhibitors have many advantages over conventional anti-cancer agents as following. Firstly, angiogenesis inhibitors can prevent the growth and metastasis of cancer cells simultaneously because angiogenesis is indispensable for the growth and metastasis of tumors. Secondly, the mutation of cancer cells into drug resistant phenotypes, which usually occurs owing to the heterogeneity and genetic instability of cancer cells, is not caused by angiogenesis inhibitors because they target not cancer cells, which are aneuploids, but normal endothelial cells, which are diploids. Thirdly, angiogenesis inhibitors are effective over all cancer species that absolutely require angiogenesis while conventional anti-cancer agents are effective against only limited cancer species. Lastly, because angiogenesis rarely occurs in normal adults except in special instances, for instance, wound healing and female menstruation, angiogenesis inhibitors would greatly reduce side effects, which are usual for conventional anti-cancer agents.

In addition, angiogenesis inhibitors are expected to be therapeutically effective against angiogenic diseases, such as rheumatoid arthritis, diabetic retinopathy, etc.

SUMMARY OF THE INVENTION

In the screening of angiogenesis inhibitors, inventors have found that a novel fungal strain isolated from soil produces 7,8-dihydro-xanthenone-8-carboxylic acid derivative, which inhibits angiogenesis as well as tumor growth.

Therefore, the present invention provides a novel 7,8-dihydro-xanthenone-8-carboxylic acid derivative represented by the chemical formula 1.

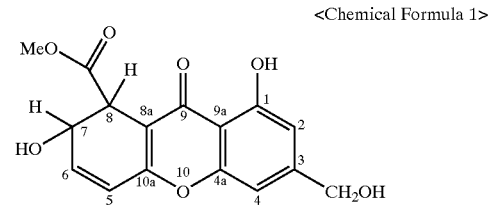

<Chemical Formula 1>

The present invention provides a novel microorganism, Aspergillus sp. Y80118 (Accession No: KCTC 0737BP).

The present invention also provides a method for preparing a 7,8-dihydro-xanthenone-8-carboxylic acid derivative from Aspergillus sp. Y80118 (Accession No: KCTC 0737BP).

The present invention also provides a use of 7,8-dihydro-xanthenone-8-carboxylic acid derivative as an inhibitor of VEGF (vascular endothelial growth factor) function or angiogenesis.

The present invention further provides pharmaceutical compositions comprising the 7,8-dihydro-xanthenone-8-carboxylic acid derivative as a pharmaceutically active ingredient for the treatment of angiogenic diseases.

●: control, ○:30 mg/kg, ▼:15 mg/kg, ▽: 5 mg/kg

Figure 3:
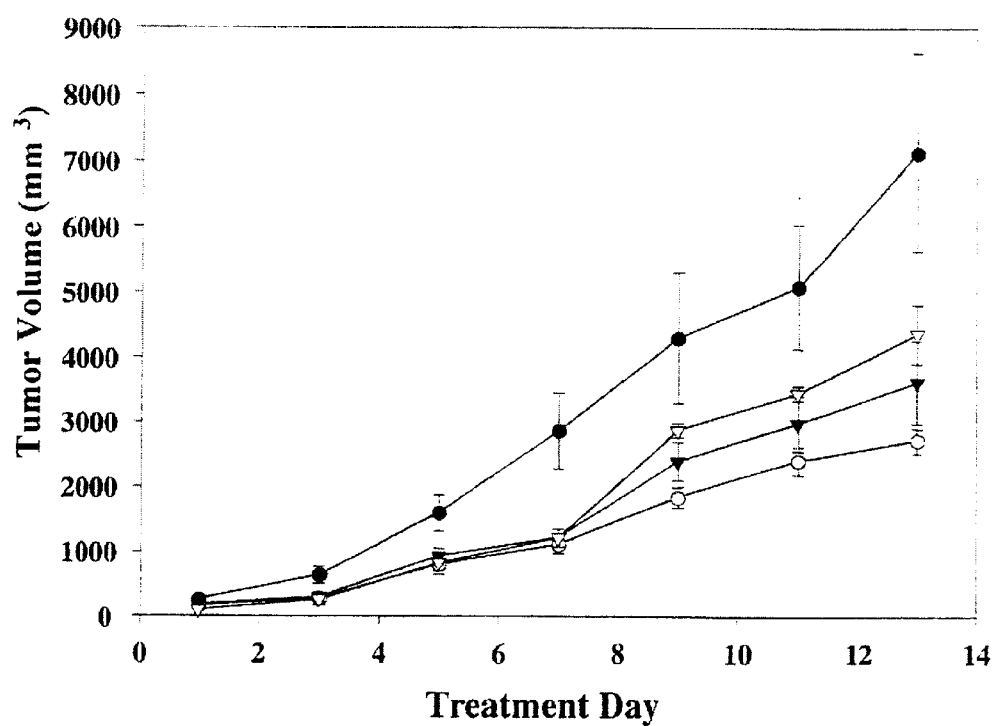

FIG. 3 shows inhibitory activity of the compound of Chemical Formula 1 against the growth of B16/BL6 melanoma.

●: control, ○:30 mg/kg, ▼:15 mg/kg, ▽:5 mg/kg

DETAILED DESCRIPTION OF PREFERRED EMBODIMENTS

The present invention is directed to the production of a novel compound useful for the inhibition of angiogenesis from a novel Aspergillus sp.

Accordingly, Aspergillus sp. Y80118 (Accession No: KCTC 0737BP) is provided.

In response to angiogenic factors, such as VEGF and bFGF, HUVEC (human umbilical vein endothelial cells) proliferate. Thus inhibition of VEGF-induced proliferation of HUVECs can be used as an index to discover a new angiogenesis inhibitor from secondary metabolites of microorganisms. By taking advantage of the VEGF-induced proliferation, a novel microorganism with fungal traits was isolated from soil and found to belong to Aspergillus. This Aspergillus sp. is similar to Aspergillus deflectus Fennell and Raper 1955 in morphology, but characterized of the production of a novel 7,8-dihydro-xanthenone-8-carboxylic acid derivative and the secretion of large quantities of yellowish brown exudate on a Czapek yeast extract agar. Thus, the isolated Aspergillus sp. was found to be a novel species which has not yet been reported, and was named Aspergillus sp. Y80118 and deposited in the Korean Collection for Type Culture of Korea Research Institute of Bioscience and Biotechnology (KRIBB) under the Accession No: KCTC 0737BP on Feb. 18, 2000.

Also, the present invention pertains to the novel compound represented by the chemical formula 1 produced from Aspergillus sp. Y80118.

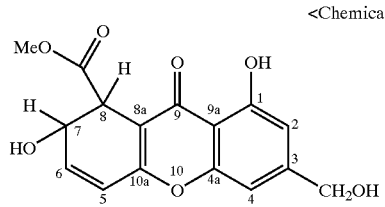

<Chemical Formula 1>

In this regard, the response of HUVEC to angiogenic factors, such as VEGF, bFGF, etc. is useful to isolate the compound, which inhibits angiogenesis. A compound isolated from the Aspergillus sp. Y80118 was found to be inhibitory against the VEGF-induced proliferation of HUVEC and to have the structure represented by the chemical formula 1 through instrumental analysis, and named ACRL-B4.

Herein, it should be noted that the novel compound ACRL-B4 may be either an optically active one, that is, an enantiomer, represented by the following chemical formula 2 or 3, or a racemate thereof. Therefore, its optically active forms and racemate all are included within the scope of the present invention.

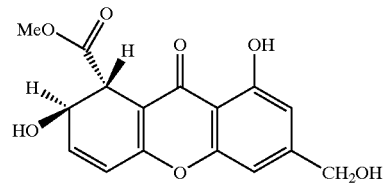

<Chemical Formula 2>

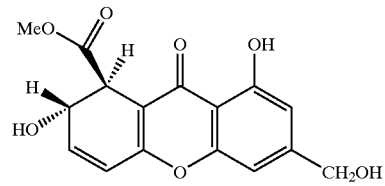

<Chemical Formula 3>

In chemical structure, the novel compound ACRL-B4 of the present invention is similar to sydowinin A (Hamasaki et al., Agr. Biol. Chem. 39:2337–2340, 2341–2345, 1975) and sydowinin B, which has reported as an inhibitor of smooth muscle myosin light chain kinase (Nakanishi et al., *J. Antibiotics*, 46:1775–1781, 1993). In particular, MS-347a, reported together with sydowinin B, having an epoxide bond instead of the double bond between positions 1 and 2 of sydowinin B, is known to have inhibitory activity against smooth muscle myosin light chain kinase as well as protein kinase C (Nakanishi et al., supra). Based on this fact, the novel compound ACRL-B4 is also expected to have inhibitory activity against kinases, especially, protein tyrosine kinase of KDR, a receptor of VEGF (vascular endothelial growth factor).

Also, the present invention pertains to a method for producing a 7,8-dihydro-xanthenone-8-carboxylic acid derivative using the novel Aspergillus sp. The production of the 7,8-dihydro-xanthenone-8-carboxylic acid derivative is accomplished by;

1) culturing Aspergillus sp. Y80118 and destroying its mycelia,
2) extracting compounds from the destroyed mycelia by use of an organic solvent, and
3) isolating and purifying the extract through chromatography.

Aspergillus sp. Y80118 can be cultured in ordinary media without requiring special conditions. The culture containing destroyed mycelia of Aspergillus sp. Y80118 is concentrated, after which the concentrate is extracted with an organic solvent in accordance with an ordinary method. Then, the extract is purified by column chromatography on silica gel to afford an active fraction. Further purification is done on the active fraction through HPLC (high performance liquid chromatography) to give a 7,8-dihydro-xanthenone-8-carboxylic acid derivative.

In an embodiment of the present invention, Aspergillus sp. Y80118 is cultured in a medium containing 2.0% glucose, 0.2% yeast extract, 0.5% polypeptone, 0.05% $MgSO_4$ and 0.1% $KH_2PO_4$, followed by adding acetone to the culture to destroy the mycelia. The culture are concentrated and extracted with ethylacetate. The ethyl acetate extract is subjected to column chromatography and then HPLC to afford ACRL-B4.

Further, the present invention pertains to the use of the 7,8-dihydro-xanthenone-8-carboxylic acid derivative as a preventive or therapeutic against angiogenic diseases and as an anti-cancer agent.

Figure 1:
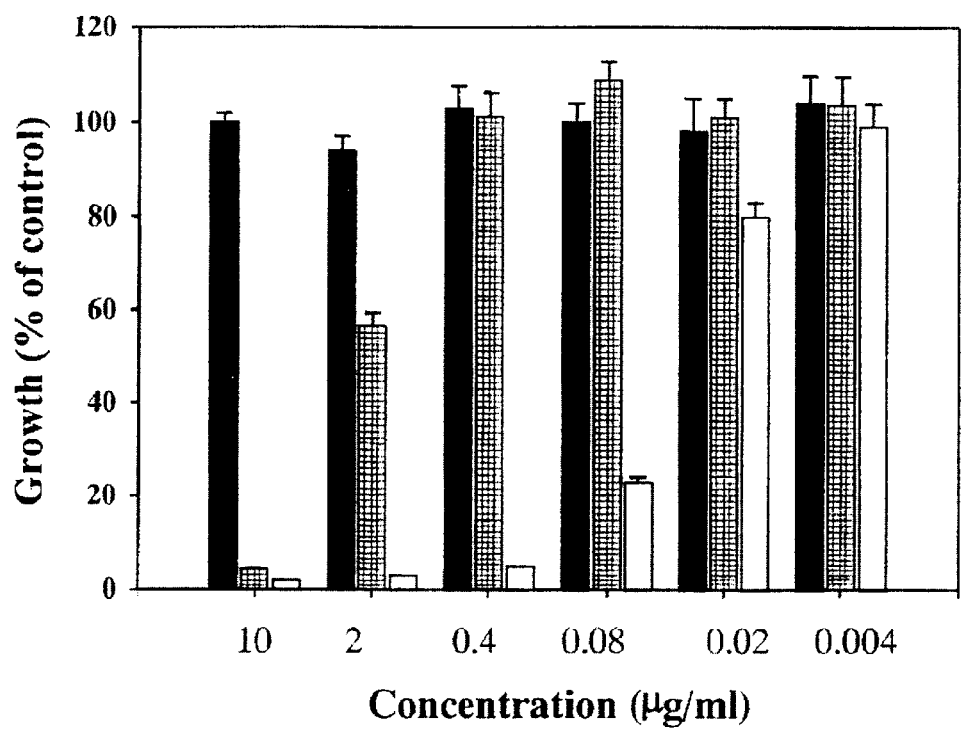
FIG. 1 is a histogram showing the inhibitory effect of the compound of Chemical Formula 1 on the proliferation of HUVEC induced by angiogenic factors.
■: control, ▦: bFGF, □: VEGF

Endothelial cells respond to angiogenic factors, such as VEGF, bFGF, etc., in the early stages of angiogenesis or neovascularization. Once stimulated by angiogenic factors, endothelial cells experience cell proliferation and differentiation after complex, intracellular reactions, which results in the induction of angiogenesis. Thus, the proliferation of vascular endothelial cells induced by VEGF, which is known to be one of the most potent angiogenic factors secreted from tumors, can be a good model to examine whether a certain compound is suppressive of angiogenesis. The effect of ACRL-B4 on the proliferation of HUVEC was tested. As a result of the examination, ACRL-B4 was found to specifically inhibit the VEGF-induced proliferation of HUVEC, as seen in FIG. 1.

A chorioallantoic membrane (CAM) assay using a fertilized egg may be useful to understand the in vivo inhibitory activity of ACRL-B4 against angiogenesis.

The novel compound ACRL-B4 of the present invention was found to inhibit angiogenesis by 71% at a dosage of 1 $\mu$g/CAM and by 90% at a dosage of 5 $\mu$g/CAM. In addition, as apparent from Table 2, the inhibition of the novel compound ACRL-B4 is comparable with that of retinoic acid as a positive control.

Also, the novel compound ACRL-B4 of the present invention was studied for in vivo anti-cancer activity using a mouse-derived Lewis lung carcinoma, 3LL cells and a melanoma B16-BL6 cells in mice.

Figure 2:
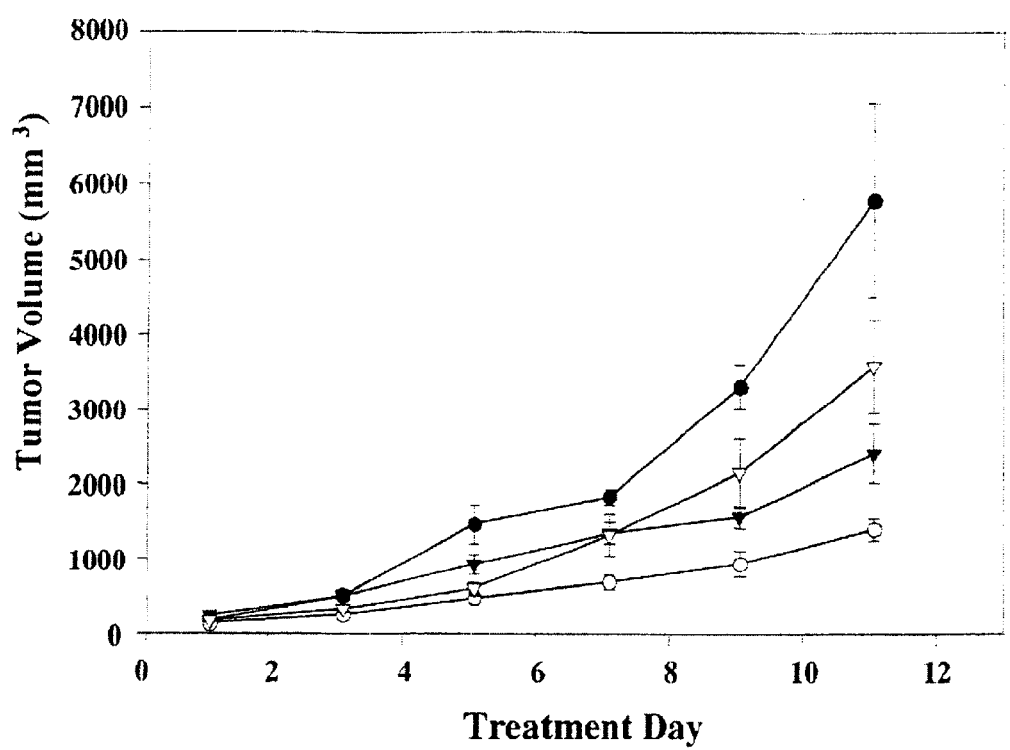
FIG. 2 shows inhibitory activity of the compound of Chemical Formula 1 against the growth of 3LL Lewis lung carcinoma.

The novel compound ACRL-B4 did not exhibit toxic effects such as weight loss on mice implanted with Lewis lung carcinoma cells and melanoma cells, and inhibited the growth of Lewis lung carcinoma cells and melanoma cells in a dose-dependent pattern, as shown in FIGS. 2 and 3.

As explained previously, the novel compound ACRL-B4 represented by the chemical formula 1 inhibits the VEGF-induced proliferation of vascular endothelial cells and exhibits potent anti-cancer activity. Therefore, the compound ACRL-B4 would be useful as a preventive or therapeutic for angiogenic diseases and as an anti-cancer agent and as a lead compound in the synthesis of angiogenesis inhibitor.

Finally, the present invention pertains to a pharmaceutical composition comprising the 7,8-dihydro-xanthenone-8-carboxylic acid derivative as a pharmaceutically effective ingredient, suitable for use in the prophylaxis and treatment of angiogenic diseases.

The term "angiogenic diseases" as used herein means various diseases and disorders in the pathogenesis of which angiogenesis plays an important role, and particularly including cancers, rheumatoid arthritis, and diabetic retinopathy.

In animal tests using mice to which mouse-derived lung cancer cells and melanoma cells were transplanted, the compound ACRL-B4 represented by the chemical formula 1 exhibited excellent anti-cancer activity, without side effects such as weight loss.

The compound of the present invention may be administered via an oral and a parenteral route in common dosage forms. They may be used in combination with a variety of conventional anti-cancer agents, such as anthracyclin compounds, taxol, etoposide, camptothecins, 5-fluorouracil, methatrexate, platinum complexes, etc., to reduce the toxicity of these anti-cancer agents and boost the therapeutic efficiency. The therapeutic compound may be also administered in combination with non-steroidal drugs for the treatment of rheumatoid arthritis or conventional drugs for the treatment of diabetic retinopathy.

As mentioned above, the compound of the present invention may be administered in various dosage forms, which are suitable to be administered via oral or parenteral routes. For this, it can be formulated along with pharmaceutically acceptable diluents or expedients, such as fillers, bulking agents, binders, wetting agents, disintegrating agents, surfactants, etc. For example, when they are to be formulated into solid forms, these are exemplified by tablets, pills, troches, powders, granules, capsules, or other dosage forms for oral administration. To prepare these solid dosage forms, ACRL-B4 may be added with at least one of expedients, such as starch, calcium carbonate, sucrose, lactose and/or gelatin. Apart from simple expedients or carriers, lubricants, such as magnesium stearate, may be added for the formulation of the compounds. Useful as liquid forms to the oral administration of the compounds are suspensions, emulsions, syrups and other usually used dosage forms for internal use. In this regard, not only simple diluents, such as water and liquid paraffin, but also various expedients, such as wetting agents, sweeteners, aromatic agents, preservatives, etc., may be used. Dosage forms for parental administration are exemplified by sterilized aqueous solutions for, for example, injection, non-aqueous solvents, suspensions, emulsions, freeze-dried agents, suppositories, etc. Examples of available non-aqueous solvents and suspensions include propylene glycol, polyethylene glycol, vegetable oils such as olive oil, and injectable esters such as ethyloleate. For the preparation of suppositories, witepsol, Macrogol, tween 61, cocoa butter, glycerol and gelatin may be used.

Depending on the ages, body conditions and body weights of the patients, the pharmaceutically effective dosage of the compound ACRL-B4 of the present invention may be varied and will in general be in the range of 1 to 50 mg/kg of body weight per day or preferably 5 to 30 mg/kg per day. Within such daily effective dosage ranges, the compounds may be administered one or more times a day. For example, a dosage unit of the compounds of the present invention may contain the same amount as the daily effective dosage, or half, one-third, or one-fourth of the daily effective dosage.

A better understanding of the present invention may be obtained in light of the following examples, which are set forth to illustrate, but are not to be construed to limit the present invention.

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1

Isolation and Identification of Novel Aspergillus sp. Y80118

Soils, taken from mountains located at Yusung, Chungchung Nam-Do, Korea, were dissolved in distilled water and the supernatant was spread over malt extract agars. After 10 days of incubation, a microorganism, which inhibits VEGF-induced HUVEC proliferation was appeared as greenish grey colony, and named strain Y80118.

Exhibiting traits of Aspergillus fungi, colonies of the isolated strain Y80118 was grown to a size of 1.4–1.9 cm at 25° C., and to a size of 2.0–2.6 cm at 37° C. for 10 days on 2% malt extract agars. The colonies were tinged with light greenish grey on their top surface with the bottom surface appearing yellowish brown, and no exudates were secreted therefrom. After incubation on Czapek yeast extract agars for 10 days, the strain Y80118 was grown, forming colonies of 1.4–2.2 cm at 25° C., and 2.8–3.0 cm at 37° C. The colonies had grey white on their top and a reddish brown central area of the bottom was surrounded by a yellowish brown perimeter. On this medium, exudates were secreted in large quantities.

Conidia of the strain were globular with a diameter of 2.4–2.8 μm. Their surface was slick and transparent in the early stage, but became somewhat uneven and rugged with a reddish brown color after the maturation of the spores.

Although such morphological traits are similar to those of Aspergillus deflectus Fennell and Raper 1955, the strain Y80118 is determined to be a variant of Aspergillus spp., a clearly novel strain. The Aspergillus sp. Y80118 was deposited in the Korean Collection for Type Culture of Korea Research Institute of Bioscience and Biotechnology (KRIBB) under the Accession No: KCTC 0737BP on Feb. 18, 2000.

Example 2

Production of Novel Compound 7,8-Dihydro-Xanthenone-8-Carboxylic Acid Methyl Ester In order to obtain a compound which can inhibit the proliferation of HUVEC, the Aspergillus sp. Y80118 isolated in Example 1 was cultured at 28° C. for 7 days in 6 liters of a medium containing 2.0% glucose, 0.2% yeast extract, 0.5% polypeptone, 0.05% $MgSO_4$, and 0.1% $KH_2PO_4$. After addition of 6 liters of acetone to destroy mycelia, the culture was concentrated, and extracted with ethyl acetate.

The ethyl acetate extract thus obtained was separated by column chromatography on silica gel eluting with a mixture of methylene chloride and methanol in volume proportions of 20:1 to afford an active fraction. After the active fraction was further purified by HPLC eluting with a mixture of methanol:water (30:70), 650 mg of a compound represented by the chemical formula 1 was obtained, which was found to have potent inhibitory activity against the proliferation of HUVEC. This compound was named ACRL-B4.

Example 3

Structural Analysis of Novel Compound 7,8-Dihydro-Xanthenone-8-Carboxylic Acid Methyl Ester For identification, the compound 7,8-dihydro-xanthenone-8-carboxylic acid methyl ester was analyzed through NMR (nuclear magnetic resonance spectroscopy), MS (mass spectroscopy), and UV-visible light spectroscopy. The physicochemical properties of the compound, disclosed through MS and UV-visible light spectroscopy, are as follows. $^1$H- and $^{13}$C-NMR data are given in Table 1, below.

mp 166–168° C.

UV λmax (MeOH):208, 271, 343 nm

EIMS m/z:318 (M+)

TABLE 1

| Location | δH | δC |
|---|---|---|
| 1 | | 161.5 |
| 2 | 6.78 (br, s) | 109.7 |
| 3 | | 152.5 |
| 4 | 7.01 (br, s) | 105.7 |
| 4a | | 157.1 |
| 5 | 6.52 (d, J = 9.9) | 123.2 |
| 6 | 6.66 (dd, J = 9.9, 4.8) | 140.6 |
| 7 | 4.71 (dd, J = 4.8, 3.6) | 65.8 |
| 8 | 4.15 (d, J = 3.6) | 46.2 |
| 8a | | 111.6 |
| 9 | | 182.5 |

TABLE 1-continued

| Location | δH | δC |
|---|---|---|
| 9a | | 110.4 |
| 10a | | 160.8 |
| 11 | 4.67 (s) | 64.3 |
| 12 | | 172.8 |
| 13 | 3.70 (s) | 53.2 |

Through the instrumental analysis, the compound obtained from Aspergillus sp. Y80118 was identified as 7,8-dihydro-1,7-dihydroxy-3-hydroxymethyl-xanthenone-8-carboxylic acid methyl ester.

Example 4

Measurement of 7,8-Dihydro-Xanthenone-8-Carboxylic Acid Derivative for Anti-Angiogenesis and Anti-Cancer Activity <4-1> Inhibitory Activity Against VEGF-Induced HUVEC Proliferation To determine the inhibitory effect of the compound represented by the chemical formula 1 on angiogenesis, endothelial cells were used as a model on the basis that they are migrated and differentiated into capillary tubes under a specific culture condition, that is, in the presence of angiogenic factors such as VEGF, bFGF, etc. Stimulation by angiogenic factors triggers complex, intracellular reactions of endothelial cells and causes them to undergo cell proliferation and differentiation, resulting in the induction of angiogenesis. Thus, the proliferation of vascular endothelial cells induced by VEGF is used to examine whether a certain compound inhibits angiogenesis. In gelatin-coated 96-well plates, HUVEC cultured in an M199 medium (20% FBS, 3 ng/ml bFGF, 100 μg/ml heparin) was plated at a density of $10^4$ cells/well and cultured for 24 hours under the condition of serum starvation. Thereafter, VEGF and bFGF were independently added at a concentration of 20 ng/ml per well and ACRL-B4 was also added at concentrations of 0.004, 0.02, 0.08, 0.4, 2 and 10 μg/ml while control wells were treated with angiogenic factors only. After 48 hours incubation, the inhibition of HUVEC proliferation by the ACRL-B4 was quantitatively analyzed by an acid phosphatase assay. The results are shown in FIG. 1.

As seen in FIG. 1, ACRL-B4 of the present invention was found to inhibit the HUVEC proliferation induced by angiogenic factors, especially VEGF. With this specific inhibition activity against VEGF-induced HUVEC proliferation, ACRL-B4 can be effectively used for the prophylaxis and treatment of angiogenic diseases.

<4-2> Inhibitory Effect on in vivo Angiogenesis Chorioallantoic membrane assay using fertilized eggs was used to examine whether the novel compound ACRL-B4 of the present invention is effective to inhibit angiogenesis in vivo.

After being grown at 37° C. for three days at a humidity of 90% in an incubator, fertilized eggs were deprived of 2 ml of albumin through a 18-gauge subcutaneous injection needle. On the fourth day, a circular window was cut into each of the eggs and the outer layers of their chorioallantoic membranes were removed. Separately, pieces of thermanox coverslip were coated with the ACRL-B4 compound dissolved in ethanol at the concentration of 1 and 5 μg/coverslip and the ethanol was evaporated. On day 4.5, the thermanox coverslip were placed on the embryonic chorioallantoic membranes of the embryos. After 2 days incubation at 37° C., 1–2 ml of 10% fat emulsion was injected into chorioallantois and observed blood vessel formation during an embryogenesis or development procedure under a microscope. As a positive control, 1 μg/egg of retinoic acid was used and a negative control was non-treated coverslip. When the CAM showed avascular zone to similar degree of retinoic acid treated CAM, the response was scored as positive, and calculated by the percentage of positive eggs to total numbers of tested eggs. The results are given in Table 2, below.

TABLE 2

| Chemical | Concentration (µg/egg) | No. of egg tested in CAM assay | No. of egg showing anti-angiogenesis | Inhibition ratio (%) |
|---|---|---|---|---|
| Negative control | | 20 | 3 | 15.0 |
| Positive control | 1 | 8 | 6 | 75 |
| ACRL-B4 | 1 | 14 | 10 | 71.4 |
| | 5 | 10 | 9 | 90 |

As indicated in Table 2, the novel compound ACRL-B4 of the present invention inhibited angiogenesis by 71% at a dose of 1 µg/CAM and 90% at a dose of 5 µg/CAM, From this result, it was found that the novel compound has inhibitory activity against angiogenesis, comparable with that of retionic acid.

<4-3> Inhibition of In Vivo Tumor Growth in Mice

The compound ACRL-B4 of the present invention was assayed for anti-cancer activity.

Into the backs of C57BL/6 mice 4–5 weeks old, $10^6$ 3LL cancer cells (Korean Collection for Type Culture at Korea Research Institute of Bioscience and Biotechnology) were subcutaneously transplanted. When the tumors were grown to sizes of 100–250 mm$^3$, the mice were randomly mixed and divided into 4 groups, each of 6 members, to which drugs were administered. For Group 1, only a solvent was used, while the novel compound ACRL-B4 represented by the chemical formula 1 was intraperitoneally injected every other day at doses of 30 mg/kg, 15 mg/kg and 5 mg/kg to Groups 2 to 4, respectively, under the monitoring of tumor sizes and body weights. The test compound was dissolved in a solvent mixture of 85% physiological saline, 5% DMSO (dimethylsulfoxide) and 10% cremophore.

Tumor sizes were calculated according to the following mathematical formula 1, and since the transplantation of cancer cells, changes in tumor size had been measured and the results are depicted in FIG. 2.

$$\text{Tumor Size (mm}^3\text{)} = \frac{[\text{Length of Longest Axis (mm)} \times \text{Length of Shortest Axis(mm)}]^2}{2}$$

<Mathematical Formula 1>

It was observed that the novel compound ACRL-B4 of the present invention inhibited the growth of Lewis lung carcinoma 3LL cells in C57BL/6 mice in a dose-dependent pattern without causing side effects such as loss of body weight. In detail, the growth of the tumor cells was inhibited by 80% at a dose of 30 mg/kg, by 60% at a dose of 15 mg/kg and by 40% at a dose of 5 mg/kg, as shown in FIG. 2.

<4-4> Inhibition of In Vivo Tumor Growth in Mice

The compound ACRL-B4 of the present invention was assayed for anti-cancer activity.

Onto the back of C57BL/6 mice 4–5 weeks old, $10^6$ B16-BL6 melanoma cells were subcutaneously transplanted. When the tumors were grown to sizes of 100–250 mm$^3$, the mice were randomly mixed and divided into 4 groups, each of 6 members, to which drugs were then administered. For Group 1, only a solvent was used, while the novel compound ACRL-B4 represented by the chemical formula 1 was intraperitoneally injected every other day at doses of 30 mg/kg, 15 mg/kg and 5 mg/kg to Groups 2 to 4, respectively, with monitoring of tumor sizes and body weights. The test compound was dissolved in a solvent mixture of 85% physiological saline, 5% DMSO (dimethylsulfoxide) and 10% cremophore.

For the calculation of cancer sizes, the mathematical formula 1 was used, and since the transplantation of cancer cells, changes in tumor size had been measured and the results are depicted in FIG. 3.

It was observed that the novel compound ACRL-B4 of the present invention inhibited the growth of melanoma B16-BL6 in C57BL/6 mice in a dose-dependent pattern without causing side effects such as loss of body weight. In detail, the growth of the cancer cells was inhibited by 65% at a dose of 30 mg/kg, by 50% at a dose of 15 mg/kg and by 40% at a dose of 5 mg/kg, as shown in FIG. 3.

Example 5

Acute Toxicity Test On Rat Upon Oral Administration

Using specific pathogen-free (SPF) SD rats, which were six weeks old, the 7,8-dihydro-xanthenone-8-carboxylic acid derivative of the present invention were tested for acute toxicity.

Suspensions of the compound of the present invention in 0.5% methyl cellulose were orally administered once at a dose of 500 mg/kg/15 ml to the rats, which were grouped in threes. After the administration, the animals were observed as to whether they died, which clinical symptoms they showed and how their weights were changed; and serologically and serobiochemically tested. An autopsy was made of the rats with the naked eye to observe whether their abdominal and thoracic organs were damaged. Neither sudden death nor noticeable clinical symptoms were detected in any of the animals administered with the compounds of interest. In addition, no toxicity signs were observed in terms of weight change, serological tests, serobiochemical tests, and corpse examination. The compounds tested caused no toxic changes rats to the rats at a dosage of 1 g/kg and thus, were found to be safe compounds with a lethal dose ($LD_{50}$) of at least 500 mg/kg when being administered via an oral route.

As described hereinbefore, the novel compound ACRL-B4 of the present invention is so high in suppressive activity against angiogenesis without side effects in vivo that it can be effectively used for the medical treatment of angiogenic diseases, including cancers, rheumatoid arthritis, and diabetic retinopathy.

The present invention has been described in an illustrative manner, and it is to be understood that the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

INDUSTRIAL APPLICABILITY

The 7,8-dihydro-1,7-dihydroxy-3-hydroxymethyl-xanthenone-8-carboxylic acid derivative of the present invention can be effectively used for the medical treatment of angiogenic diseases, including cancers, rheumatoid arthritis, and diabetic retinopathy.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. 7,8-dihydro-1,7-dihydroxy-3-hydroxymethyl-xanthenone-8-carboxylic acid derivative, represented by the following chemical formula

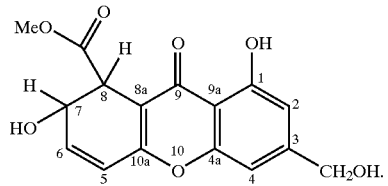

2. The pharmaceutical composition for the prophylaxis and the treatment of angiogenic diseases, comprising A use of 7,8-dihydro-1,7-3-hydroxymethyl-xanthenone-8-carboxylic acid derivative.

3. The pharmaceutical composition of claim 2, wherein the angiogenic diseases are selected from the group consisting of cancer, rheumatoid arthritis, and diabetic retinopathy.

4. The pharmaceutical composition of claim 2, further comprising a pharmaceutically acceptable diluent.

* * * * *

UNITED STATES PATENT AND TRADEMARK OFFICE
CERTIFICATE OF CORRECTION

PATENT NO. : 6,770,671 B2
DATED : August 3, 2004
INVENTOR(S) : Jung Joon Lee et al.

It is certified that error appears in the above-identified patent and that said Letters Patent is hereby corrected as shown below:

Column 12,
Line 11, "The" should read -- A --;
Line 12, "A use of" should be deleted;
Line 13, "1,7-3-hydroxymethyl" should read -- 1,7-dihydroxy-3-hydroxymethyl --.

Signed and Sealed this

Nineteenth Day of October, 2004

JON W. DUDAS
*Director of the United States Patent and Trademark Office*